United States Patent [19]

Jambor

[11] Patent Number: 4,786,285
[45] Date of Patent: Nov. 22, 1988

[54] OSTOMY APPLIANCE AND COUPLING RING ASSEMBLY THEREFOR

[75] Inventor: Ferenc Jambor, Gurnee, Ill.

[73] Assignee: Hollister Incorporated, Libertyville, Ill.

[21] Appl. No.: 943,130

[22] Filed: Dec. 18, 1986

[51] Int. Cl.⁴ ............................................. A61F 5/44
[52] U.S. Cl. .................................. 604/342; 604/339; 383/63
[58] Field of Search ...................... 604/277, 332–345, 604/355; 383/63–66; 150/55; 220/306, 307

[56] References Cited

U.S. PATENT DOCUMENTS

| | | | |
|---|---|---|---|
| Re. 28,969 | 9/1976 | Naito | 150/3 |
| 2,144,755 | 1/1939 | Freedman | 24/201 |
| 2,581,604 | 1/1952 | Roehrl | 24/201 |
| 2,752,972 | 7/1956 | Tupper | 150/5 |
| 2,823,720 | 2/1958 | Svec | 150/3 |
| 2,994,117 | 8/1961 | McMullin | 24/201 |
| 3,528,420 | 9/1970 | Nielson | 604/342 |
| 3,732,909 | 5/1973 | Rooke et al. | 220/306 |
| 3,898,990 | 8/1975 | Nolan | 604/336 |
| 3,977,563 | 8/1976 | Holt | 220/306 |
| 4,232,672 | 11/1980 | Steer et al. | 604/338 |
| 4,419,100 | 12/1983 | Alexander | 604/341 |
| 4,460,363 | 7/1984 | Steer | 604/336 |
| 4,555,043 | 11/1985 | Bernhardt | 220/306 |
| 4,586,927 | 5/1986 | Jensen | 604/342 |
| 4,592,750 | 6/1986 | Kay | 604/342 |
| 4,610,676 | 9/1986 | Schneider | 604/339 |
| 4,648,875 | 3/1987 | Ferguson | 604/339 |

FOREIGN PATENT DOCUMENTS 3243097 5/1984 Fed. Rep. of Germany ...... 220/306

Primary Examiner—C. Fred Rosenbaum
Assistant Examiner—Mario Costantino
Attorney, Agent, or Firm—Tilton, Fallon, Lungmus

[57] ABSTRACT

An ostomy appliance in which the coupling ring assembly that detachably joins the faceplate and pouch of the appliance takes the form of a pair of flexible plastic rings, each ring being generally C-shaped in radial cross-section and defining an axially-facing annular channel. One of the rings is nested within the channel of the other ring when the rings are coupled together, with the inner and outer rings having opposing surfaces that sealingly engage each other and together define at least one circumferentially-extending fluid-isolating reservoir.

7 Claims, 2 Drawing Sheets

OSTOMY APPLIANCE AND COUPLING RING ASSEMBLY THEREFOR

BACKGROUND AND SUMMARY

As brought out in co-owned U.S. Pat. No. 4,610,676, an important requirement for what are now commonly referred to as "two-piece" ostomy appliances is that their coupling rings be capable of flexing and deforming to conform with changes in the peristomal contour of a patient's body as that patient bends, twists, and moves about. It is also essential that such conformity be achieved without risk that the coupling rings will become unintentionally disconnected or that leakage of fluids (liquids or gases) might occur. Other considerations include ease of attachment and flatness of profile. The ideal coupling ring assembly should be flat enough so the fact that a patient is wearing an ostomy appliance beneath his/her clothing is virtually undetectable.

Ostomy appliances are known in which one coupling ring has an axially-facing annular channel and the other ring has a rib or projection insertable therein. Reference may be had to U.S. Pat. No. 4,460,363 and the patents cited in it. U.S. Pat. No. Re. 28,969 reveals that interlocking elements, one being channel-shaped and the other having a rib or projection receivable in the channel, have also been used to connect plastic films together along linear zones of attachment, and other patents such as U.S. Pat. Nos. 2,752,972 and 3,977,563 disclose similar interlocking arrangements used for replaceable container lids. Additional patents representative of the prior art are U.S. Pat. Nos. 2,994,117, 2,823,720, 2,144,755, and 2,581,604.

While two-piece ostomy appliances with coupling rings of various constructions have been known and used features included to meet certain of the requirements discussed above often reduce the capability of the appliances to meet other such requirements. For example, increased security of attachment might be achieved at the expense of reduced flexibility. Accordingly, it is an object of this invention to provide a coupling ring construction that results in a secure interconnection between the parts—one that resists fluid leakage as well as unintentional detachment—and, at the same time, is relatively flat, compact, and flexible.

The coupling rings of this invention are formed of flexible plastic material with the wall of each ring being generally C-shaped when viewed in radial cross-section. In coupled condition, one ring, which may be referred to as the inner ring, is nested within the channel of the other ring (the outer ring). The walls of the inner and outer rings have their opposing surfaces sealingly engaging each other; however, the sealing contact is along circumferentially-extending zones of contact with circumferentially-extending fluid-isolating reservoirs therebetween. Because of the reduced areas of surface contact, greater unit pressure and improved sealing effectiveness are achieved. Of particular importance is the fact that any fluid entering one of the reservoirs tends to become entrapped therein, with migration permitted in circumferential directions rather than axial directions. As a result, the coupling ring assembly is notably resistant to fluid leakage despite the ease with which it may be flexed or deformed.

Other features, advantages, and objects of the invention will become apparent from the specification and drawings.

DRAWINGS

DETAILED DESCRIPTION OF PREFERRED EMBODIMENT

Figure 1:
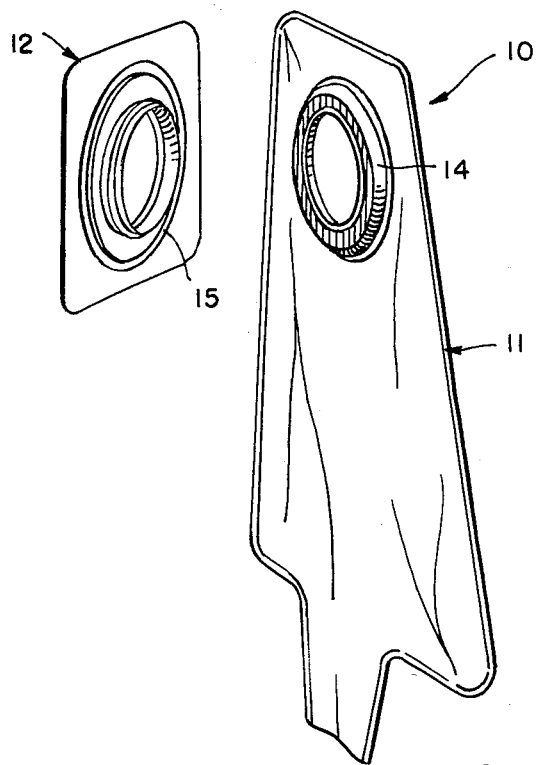
FIG. 1 is a perspective view of a two-piece ostomy appliance embodying the invention, the faceplate assembly being shown detached from the pouch assembly.

Referring to FIG. 1, the numeral 10 generally designates an ostomy appliance composed essentially of a collection pouch 11, a faceplate 12, and a coupling ring assembly 13 (FIG. 2) consisting of a pouch coupling ring 14 and a faceplate coupling ring 15. Both the pouch and faceplate may vary considerably in size, shape, and construction, all as well known in the art, and it is to be understood that the coupling ring assembly is not limited in its use to the particular pouch and faceplate constructions shown in the drawings. For example, pouch 11 is shown to have an outlet 16 at its lower end, such outlet being intended to be closed by a suitable clamping device (not shown) such as the one disclosed in U.S. Pat. No. 3,523,534; however, the pouch may if desired be "non-drainable," in which case outlet 16 would be omitted. Typically, pouch 11 is designed to be relatively flat and is composed of two sheets or walls 11a and 11b of flexible thermoplastic film that are heat sealed together along their margins as indicated at 17 in FIG. 2.

Faceplate 12, in the particular form illustrated in the drawings, is constructed generally in accordance with the teachings of U.S. Pat. No. 4,213,458, and reference may be had to that patent for information on the details of construction. Faceplate 12 includes a highly flexible patch or panel 18 of gas-penetrable but water-resistant microporous material. Various materials having such properties are known and may be used. The faceplate should be highly flexible so that it will conform readily to body contours and body movements, and be coated on its back or rear side with a medical-grade pressure-sensitive adhesive so that upon removal of backing sheet or sheets 19 the microporous adhesive-coated patch or panel 18 may be secured to the patient's skin in the peristomal region.

An attaching ring or collar 20 may be secured to the front face of the microporous patch 18 by heat sealing or by any other suitable means. The attaching ring must also be capable of being heat sealed or otherwise securely joined, either directly or indirectly, to the faceplate coupling ring 15. In the construction depicted in the drawings, such connection is indirect to the extent that a web 21 of thin, flexible, and resilient thermoplastic material is interposed between the faceplate ring 15 and the attaching ring 20, as generally disclosed in co-owned U.S. Pat. No. 4,419,100. Specifically, the inner margin of the annular web 21 is heat sealed at 22 to the faceplate 12 and its outer margin is heat sealed at 23 to faceplate ring 15. The web gives rise to a floating relationship between the faceplate coupling ring 15 and the faceplate 12, promoting conformity of the faceplate to a wearer's body without resistance from the coupling rings and, in general, allowing limited movement of the coupling ring assembly in generally axial directions with respect to the faceplate. Such limited movement allows a user to insert his (her) fingers between the coupling ring assembly and faceplate 12 to facilitate attachment and detachment of the coupling rings without causing discomfort. The web 21 should be formed of a heat-sealable, tough, and durable material that is also capable of functioning as a fluid and odor barrier. Low density polyethylene coextruded with a coextensive layer or core of polyvinylidene chloride, known under the designation Saranex, from Dow Chemical Company, Midland, Michigan, has been found suitable but other materials having similar properties are available and ma be used.

Figure 2:
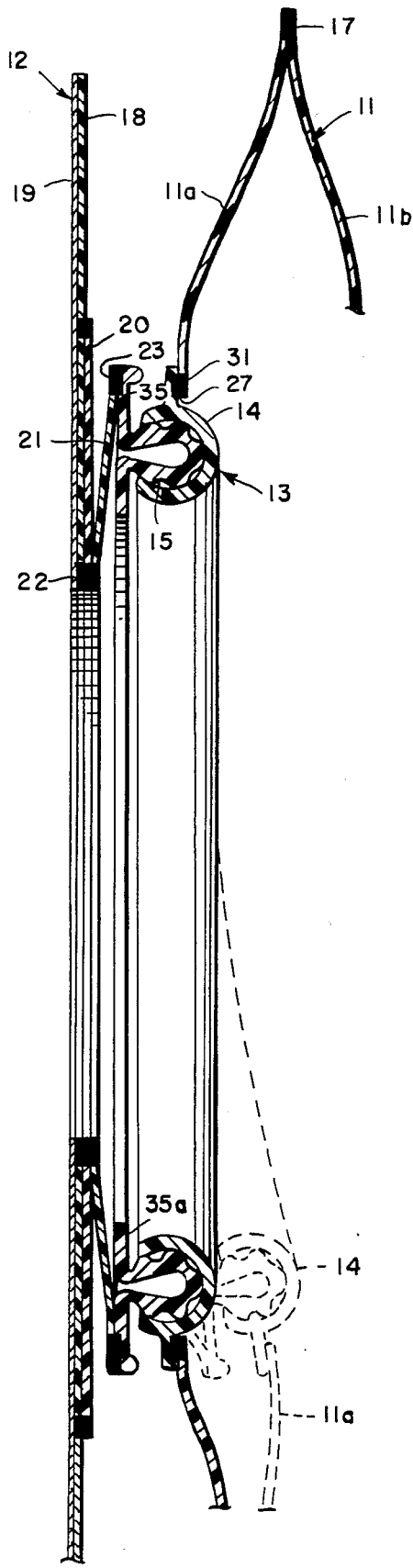
FIG. 2 is a vertical sectional view of the appliance showing the coupling rings thereof in assembled condition.
Figure 3:
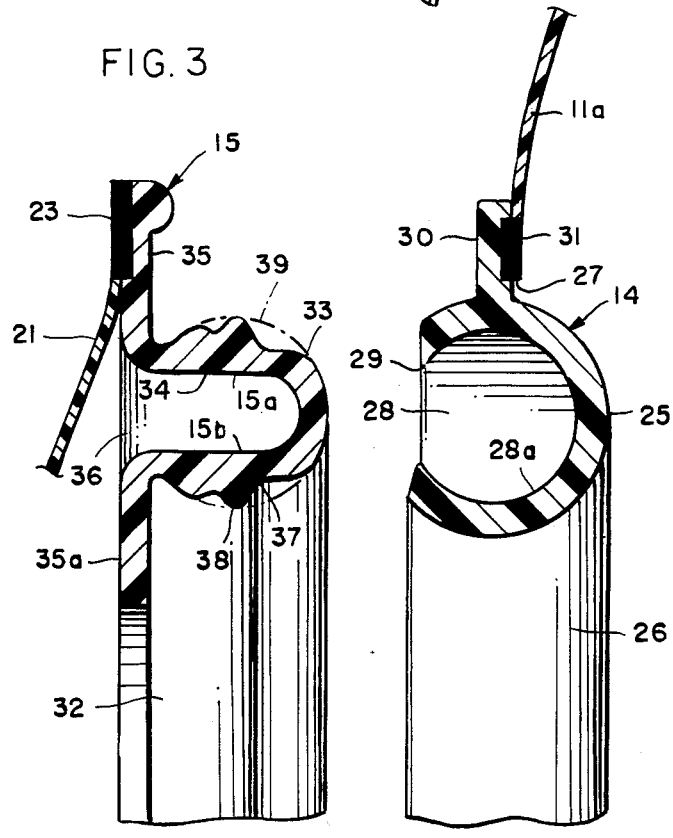
FIG. 3 is an enlarged radial cross-sectional view of the coupling rings in separated and untensioned condition.

The coupling ring assembly 13, and particularly the structural relationship between pouch coupling ring 14 and faceplate coupling ring 15, are illustrated most clearly in FIGS. 2 and 3. Ring 14 is in the form of a continuous loop with its annular wall 25 defining a central opening 26 coaxial with the opening 27 in wall 11a of the pouch When viewed in radial cross-section, wall 25 is generally C-shaped and defines a channel that faces axially away from pouch 11. The annular entrance 29 to that channel is shown in FIG. 3 to have a substantially smaller radial dimension than the interior of the channel 28 when the coupling ring is in an untensioned or undeformed state. Ring 14 also includes an outwardly-projecting annular mounting flange 30 that extends along a plane spaced from both of the axial limits of the ring—in the illustration given, the flange is approximately equidistant from both the proximal and distal axial limits of ring 14. The flange is secured by heat seal 31 or by other suitable means to the wall 11a of the pouch about pouch opening 27 and, because the flange is located along a midplane between the ring's axial limits, a substantial portion of the ring 14 projects into the interior of the pouch.

The faceplate ring 15 is also in the form of a continuous loop defining a central opening 32 alignable with the opening 26 of the pouch ring. Like the pouch ring 14, faceplate ring 15 is generally C-shaped in radial cross-section with its wall 33 defining an annular channel 34 that faces in the same axial direction as the channel 28 of pouch ring 14. A planar annular mounting flange 35 extends radially outwardly from the mouth or entry 36 of ring 15 and provides the means for heat seal attachment (at 23) to web 21. The flange 35 is also useful for the purpose of gripping ring 15 during uncoupling and coupling of the ring assembly. An inwardly-directed flange 35a (FIG. 3) may also be provided and is especially useful as the means for direct attachment to faceplate 12 in those instances where web 21 is to be omitted. Alternatively, where web 21 is included, such web may be attached to flange 35a instead of flange 35. In the particular arrangement shown, flange 35a is not so utilized and, if desired, may be reduced in size or omitted entirely.

Figure 4:
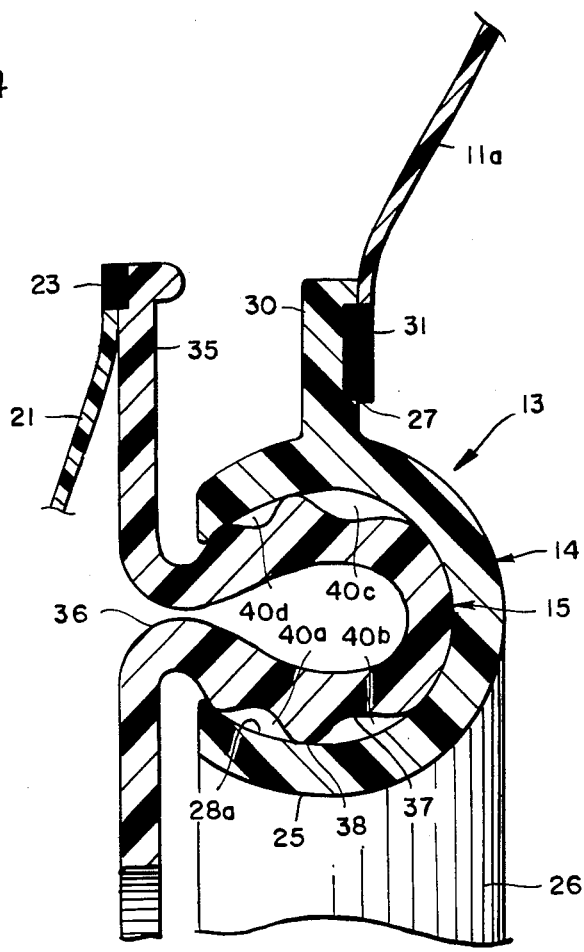
FIG. 4 is a sectional view similar to FIG. 3 but showing the rings in coupled condition.

The rings are formed of low density polyethylene or other flexible plastic material characterized by toughness, durability, and at least moderate elastic recovery. In the unflexed or untensioned condition shown in FIG. 3, faceplate ring 15 has side wall portions 15a and 15b with outer surfaces that are spaced apart (when viewed in radial cross-section) a distance substantially greater than the cross section of channel 28. When the coupling rings are assembled with the inner ring 15 nested within outer ring 14, the radially-measured distance between the outer surfaces of side walls 15a and 15b is substantially reduced with the mouth 36 of channel 34 being partially (if not completely) closed. Similarly, the width of the channel 28 of ring 14 is increased at least to a slight extent. The outer ring 14 exerts compressive forces on the inner ring 15, and the inner ring in turn exerts tensioning forces on the outer ring. The result is that the opposing surfaces of the rings are in tight sealing engagement with each other when those rings are nested as shown in FIG. 4.

One of the opposing surfaces is smoothly curved, approximating the arc of a circle when viewed in section, and the other opposing surface is undulating, being provided with ridges and grooves. The drawings illustrate a preferred construction in which the ridges and grooves are formed along the outer surface of the inner ring and the smooth arcuate bearing surface is defined by the inner surface of the outer ring. Thus, channel 28 of ring 14 is defined by a smoothly curved surface 28a which, when viewed in section, is arcuate. As shown clearly in FIG. 3, surface 28a is in the shape of an incomplete circle with a constant radius when the ring 14 is viewed in radial cross-section. The outer surfaces of side wall portions 15a and 15b of the inner ring 15 are provided with grooves or indentations 37 that extend circumferentially and result in a plurality of circumferential ridges or ribs 38 that face inwardly and outwardly in generally opposite radial directions away from ring 15, as depicted in FIG. 3. Phantom line 39 in FIG. 3 represents an extension of the curved outer surface of ring 15 bridging the crests of ridges 38 and revealing that if it were not for grooves 37, the outer surface of ring 15 would follow closely the arc of a circle when viewed in cross section. When the rings are coupled together, the rounded crests of the ridges forceably engage the inner surface 28a of outer ring 14 and, because of the reduced area of contact, a relatively high unit force is exerted between the rings to seal the parts together and prevent fluid leakage. In addition, grooves 37 result in the formation of sealed, circumferentially-extending, annular reservoirs or cavities 40a–40d between the opposing surfaces of the two rings.

Figure 5:
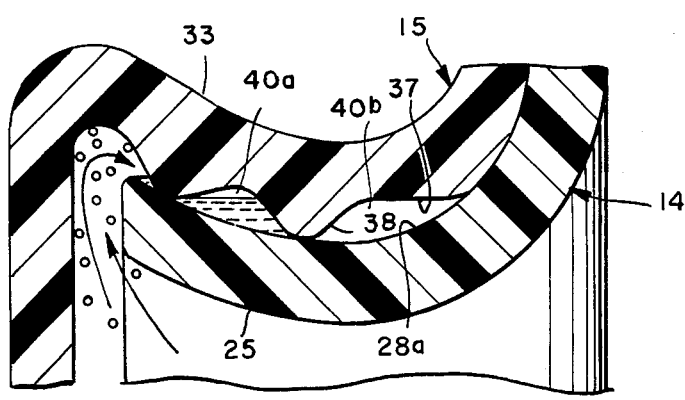
FIG. 5 is an enlarged fragmentary sectional view depicting the action of the fluid reservoirs in preventing leakage.

If the coupled rings were in a static environment, fluid would not be expected to enter any of the cavities, assuming that the surfaces of the parts were perfectly formed in manufacture and were not thereafter scratched, nicked, or otherwise damaged by the user or by others The rings are, however, used in a dynamic environment and are exposed to considerable twisting and flexing when the ostomy appliance is worn by an active patient. Also, forces on the parts are altered with changes in the volume of the contents of pouch 11. Removal and replacement of the pouch, or the substitution of a fresh pouch for a discarded one, may also result in small, perhaps even microscopic, scratches, nicks, or cuts being formed in the surfaces of the parts, particularly the surfaces of ridges 38. Under such circumstances, some liquid and gas passing through the stoma-receiving openings of the coupling rings might be expected to flow outwardly into reservoir 40a, as schematically depicted in FIG. 5. However, before failure of the seal between the coupling rings can occur, such fluid must also migrate from reservoir 40a into reservoir 40b, then into reservoir 40c and 40d, and finally escape from reservoir 40d. Since all of the reservoirs are isolated from each by the intervening circumferential ridges and the forceful contact between those ridges and the smooth inner surface of the outer coupling ring, the possibilities of such failure occurring are extremely remote if not non-existent. The result is a low-profile coupling ring assembly that is readily capable of withstanding substantial flexing and distortion, and the abuses that might be expected during normal use without fluid leakage.

Resistance to fluid leakage may be the result of other factors as well. The areas of contact between the circumferential ridges 38 and the smooth surface 28a may be regarded as capillaries which gradually expand or widen to form reservoirs 40a, 40b, 40c and 40d. The diverging surfaces of such capillaries give rise to an increase in the apparent viscosity of any liquid managing to flow into the reservoirs. In addition, the multiple ridges 38 produce what might be regarded as labyrinth seals with the fluid pressures in the reservoirs or cavities diminishing from one to the next should liquid invade more than one such cavity. If distortions or excessive radial loads cause a small break in one such seal, at a point along the circumference of one of the ridges 38, liquid at reduced pressure must travel through the entered cavity to locate a break in the seal formed by the next ridge 38, and then through each of the remaining cavities to locate similar breaks in the seals formed by the remaining ridges, before leakage through the coupling ring assembly occurs.

The pouch coupling ring has been shown and described with its channel 28 facing away from the pouch and with the faceplate ring received in that channel when the parts are coupled together. While that arrangement is particularly advantageous, it is to be understood that ring 14 might instead be mounted on the faceplate, with its channel 28 facing away from the faceplate towards the pouch, and ring 15 might instead be secured to the pouch. In either case, the two C-shaped rings are nested together when the pouch is coupled to the faceplate of the appliance.

An important aspect of this construction is that both of the C-shaped rings 14 and 15 have their concentric channels facing in the same axial direction when the rings are nested together. As a result, forces caused by twisting, flexing, and other distortions of the rings act on both of the nested rings in essentially the same way. Since the rings react in similar fashion to such distorting forces, possibilities of separation and leakage are minimized.

While in the foregoing I have disclosed an embodiment of the invention in considerable detail for purposes of illustration, it will be understood by those skilled in the art that many of these details may be varied without departing from the spirit and scope of the invention.

I claim:

1. An ostomy appliance including a pouch having a stoma opening; an adhesive faceplate having an aperture alignable with said opening; and a coupling ring assembly detachably joining said pouch and faceplate together; said coupling ring assembly including a pouch ring secured to said pouch about said opening and a faceplate ring secured to said faceplate about said aperture; said rings being formed of flexible plastic material each having an annular wall extending about a central opening; wherein the improvement comprises each of said rings having a generally C-shaped portion, when viewed in radial cross-section, defining an axially-facing channel; the C-shaped portion of one of said rings being nested and retained within the channel of the other of said rings when said rings are coupled together, with said one ring constituting an inner ring and said other ring constituting an outer ring in said nested relationship; said outer ring, when viewed in radial cross-section, having an inner surface that is smoothly curved in the shape of an incomplete circle; said inner ring, when viewed in radial cross-section, having an undulating outer surface providing a plurality of circumferential ridges that face inwardly and outwardly in generally opposite radial directions and define circumferential grooves therebetween; said ridges sealingly engaging said inner surface along generally radially opposite sides of said inner ring so that said grooves form circumferentially-extending fluid-isolating reservoirs when said rings are coupled together.

2. The appliance of claim 1 in which said inner ring is secured to said faceplate and said outer ring is secured to said pouch; said outer ring having its channel facing away from said pouch.

3. The appliance of claim 1 in which each of said ridges is rounded when viewed in radial section.

4. The appliance of claims 1, 2 or 3 in which said outer ring has an entrance opening leading to said channel thereof; the radial cross-sectional dimension of said entrance opening being less than the maximum radial cross-sectional dimension of said channel when said outer ring is in unflexed condition.

5. The appliance of claims 1, 2 or 3 in which said inner ring has an outside radial cross-sectional dimension greater than the inside radial cross-sectional dimension of said channel when said inner and outer rings are in unflexed condition.

6. The appliance of claims 1, 2 or 3 in which said outer ring includes a planar mounting flange extending radially outwardly therefrom along a plane spaced between axial limits of said outer ring; said mounting flange being sealed to said pouch about the stoma opening thereof.

7. The appliance of claims 1, 2 or 3 in which said inner ring has an entrance opening leading to the channel thereof; and a planar mounting flange extending radially outwardly from said inner ring adjacent said entrance opening; said mounting flange being connected to said faceplate.

* * * * *